US010997312B2

(12) United States Patent
Miao et al.

(10) Patent No.: US 10,997,312 B2
(45) Date of Patent: May 4, 2021

(54) ACCESS CONTROL FRAMEWORK

(71) Applicant: Microsoft Technology Licensing, LLC, Redmond, WA (US)

(72) Inventors: Yi Miao, Redmond, WA (US); Mahmood G. Qadir, Redmond, WA (US); Pritvinath Obla, Bellevue, WA (US); Pierre N. Martin, Seattle, WA (US); Anubhuti Manohar, Redmond, WA (US); Sizheng Chen, Redmond, WA (US); Vishal Mishra, Bellevue, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 628 days.

(21) Appl. No.: 15/132,109

(22) Filed: Apr. 18, 2016

(65) Prior Publication Data

US 2016/0328575 A1 Nov. 10, 2016

Related U.S. Application Data

(63) Continuation of application No. 13/291,121, filed on Nov. 8, 2011, now abandoned.

(51) Int. Cl.
*G06F 17/00* (2019.01)
*G06F 21/62* (2013.01)
*G06F 16/28* (2019.01)
*G06F 16/242* (2019.01)
*G16H 10/60* (2018.01)
*G16H 40/20* (2018.01)

(Continued)

(52) U.S. Cl.
CPC ...... *G06F 21/6245* (2013.01); *G06F 16/2433* (2019.01); *G06F 16/284* (2019.01); *G06F 19/00* (2013.01); *G06F 21/604* (2013.01); *G06F 21/6227* (2013.01); *G16H 10/60* (2018.01); *G16H 40/20* (2018.01)

(58) Field of Classification Search
None
See application file for complete search history.

(56) References Cited

U.S. PATENT DOCUMENTS 5,787,428 A 7/1998 Hart
6,275,824 B1 8/2001 O'Flaherty et al.
(Continued)

OTHER PUBLICATIONS

Ager et al. "Policy-Based management and sharing of sensitive information among government agencies", IEEE Conference on Military Communications, Oct. 2006, pp. 1-9.
(Continued)

*Primary Examiner* — Hasanul Mobin

(57) ABSTRACT

The described implementations relate to an access control framework for a database system. One implementation can receive, from a user, a request for data that identifies a resource, such as a view that obtains data from a database. The implementation can check the identity of the user to identify user roles associated with the user. The implementation can identify an access policy that is associated with the resource, and a rule that is associated with the access policy and applies to the user roles associated with the user. The rule can be applied to the request for data using attributes of the access policy. For example, if the request for data is a query on a view, the query can be rewritten to apply the rule.

20 Claims, 10 Drawing Sheets

(51) Int. Cl.
*G06F 19/00* (2018.01)
*G06F 21/60* (2013.01)

(56) References Cited

U.S. PATENT DOCUMENTS

| | | | |
|---|---|---|---|
| 7,774,365 B2* | 8/2010 | Oxenstierna | G06F 21/6218 707/783 |
| 9,037,609 B1* | 5/2015 | Tibbitts | G06F 16/258 707/783 |
| 2002/0099671 A1* | 7/2002 | Mastin Crosbie | G06Q 99/00 705/500 |
| 2002/0198961 A1* | 12/2002 | Krishnamurthy | H04L 29/06 709/217 |
| 2003/0018786 A1* | 1/2003 | Lortz | H04L 41/0893 709/226 |
| 2003/0177376 A1 | 9/2003 | Arce Velleggia et al. | |
| 2004/0019809 A1 | 1/2004 | Sheinis et al. | |
| 2004/0044905 A1 | 3/2004 | Heath et al. | |
| 2004/0215604 A1* | 10/2004 | Ivanov | G06F 16/24524 |
| 2005/0038765 A1* | 2/2005 | Sterling | H04L 41/0893 |
| 2005/0038783 A1 | 2/2005 | Lei et al. | |
| 2005/0144176 A1 | 6/2005 | Lei et al. | |
| 2005/0165799 A1* | 7/2005 | Wong | G06F 21/6227 |
| 2005/0216465 A1* | 9/2005 | Dutta | G06F 17/30306 |
| 2005/0251508 A1* | 11/2005 | Shimizu | H04L 67/1097 |
| 2006/0089932 A1 | 4/2006 | Buehler et al. | |
| 2006/0156379 A1* | 7/2006 | Vissapragada | G06F 21/552 726/1 |
| 2006/0173845 A1* | 8/2006 | Handy-Bosma | G06F 17/30448 |
| 2006/0212491 A1 | 9/2006 | Agrawal et al. | |
| 2006/0248592 A1 | 11/2006 | Agrawal et al. | |
| 2007/0143148 A1 | 6/2007 | Kol et al. | |
| 2008/0016580 A1 | 1/2008 | Dixit et al. | |
| 2008/0071785 A1* | 3/2008 | Kabra | G06F 17/30306 |
| 2009/0013401 A1 | 1/2009 | Subramanian et al. | |
| 2009/0094193 A1* | 4/2009 | King | G06F 21/6227 |
| 2009/0300002 A1* | 12/2009 | Thomas | G06F 16/2457 |
| 2010/0011031 A1* | 1/2010 | Huang | H04L 63/1425 707/E17.007 |
| 2010/0179831 A1 | 7/2010 | Brown et al. | |
| 2010/0262577 A1* | 10/2010 | Pulfer | G06F 16/93 707/608 |
| 2010/0262625 A1 | 10/2010 | Pittenger | |
| 2010/0268722 A1 | 10/2010 | Yalamanchi et al. | |
| 2010/0325717 A1* | 12/2010 | Goel | H04L 63/102 726/11 |
| 2011/0252459 A1* | 10/2011 | Walsh | H04L 63/20 726/4 |
| 2012/0233148 A1* | 9/2012 | Chen | G06F 16/24534 707/717 |
| 2013/0117313 A1 | 5/2013 | Miao et al. | |

OTHER PUBLICATIONS

Hong et al. "Preserving privacy in e-Health system using Hippocratic database", Proceedings of the 32nd annual IEEE International Computer Software and Applications Conference, 2008, pp. 692-697.
Office Action for U.S. Appl. No. 13/291,121, dated Jan. 21, 2015, Yi Miao, "Access Control Framework", 10 pages.
Office Action for U.S. Appl. No. 13/291,121, dated Oct. 16, 2015, Yi Miao, "Access Control Framework", 17 pages.
Office Action for U.S. Appl. No. 13/291,121, dated Dec. 20, 2013, Yi Miao, "Access Control Framework", 14 pages.
Office action for U.S. Appl. No. 13/291,121, dated Apr. 22, 2016, Miao et al.1, "Access Control Framework n", 22 pages.
Office Action for U.S. Appl. No. 13/291,121, dated May 10, 2013, Yi Miao, "Access Control Framework", 14 pages.
Watkins, B. "Hide sensitive data with oracle 10g column masking" Feb. 6, 2007 [online][retrieved at: http://www.techrepublic.com/article/hide-sensitive-data-with-oracle-10g-column-masking/6156626>>, 2 pps.

* cited by examiner

300

Access Policy Name: VISIT

Attributes:
    String EID (Primary Key)    // from VisitID of VisitInfo table
    String Department    // from AdmitDepartment of VisitInfo table
    String State    // from State of VisitInfo table
    String Insurance    // From InsCo of InsuranceInfo table

Roles:

Doctor in Radiology:
    Rule1:
        [VISIT].[DEPARTMENT]='Radiology'
        UNLOCK sensitive Doctor in Washington:
    Rule2:
        [VISIT].[STATE]='Washington'
        LOCK sensitive

Resources:
BV_LAB_OBR
BV_CLINICAL

Data Sources:
PV1

Entity Name: PATIENT

Attributes:
    String PatientID (Primary Key)
    String LastName
    String FirstName
    String Address
    Bool IsVIP
    String InsCo

Roles:

Doctors
   Rule1:
      [PATIENT].[IsVIP]='FALSE'

Doctor in VIP Access Group:
   Rule2:
      [PATIENT].[IsVIP]='TRUE'

Data Sources:
PV1

Entity Name: VISIT

Attributes:
    String EID (Primary Key)
    String PatientID      // bound to PatientID of Patient entity
    String Department
    String State

Roles:

Doctor in Radiology:
    Rule1:
        [VISIT].[DEPARTMENT]='Radiology'
        UNLOCK sensitive Doctor in Washington:
    Rule2:
        [VISIT].[STATE]='Washington'
        LOCK sensitive

Data Sources:
PV1

FIG. 8

ACCESS CONTROL FRAMEWORK

BACKGROUND

Database technology allows users to access vast amounts of data with relative ease. For example, users or applications can use predefined view queries that execute within a database and return results to the user, e.g., in the form of a table. However, in some contexts, it can be difficult to manage access control to data within the database. For example, in a health care context, users often have different access privileges to data in the database, e.g., nurses may not be able to access all of the data that doctors can access.

One way to implement access control in a database system is to add custom filters to the database views with which users query the database system. For example, each time a database view is defined, a database administrator can rewrite the database view so that, when the database view is executed by a user, the database view will return results to a user that are consistent with the user's access privileges. For example, a database view could be written with a first custom filter for doctors and a second custom filter for nurses. However, defining custom access filters on a view-by-view basis can be very complex, particularly when a database system needs to support a wide variety of users and a wide variety of different views.

SUMMARY

The described implementations relate to databases. One implementation can associate attributes with an access policy. The attributes can be bound to one or more data sources that provide values of the attributes. Rules can be associated with the attributes. One or more resources can be bound to the access policy to apply the rules to inputs or outputs of those resources using the values of the attributes.

Another implementation can receive a request for data from a user. The request can identify a resource. An identity of the user can be checked to identify one or more user roles that are associated with the user. An access policy associated with the resource can be identified. A rule can be identified that is associated with the access policy and applies to the one or more user roles that are associated with the user. The rule can be applied to the request using one or more attributes of the access policy.

The above listed examples are intended to provide a quick reference to aid the reader and are not intended to define the scope of the concepts described herein.

BRIEF DESCRIPTION OF THE DRAWINGS

The accompanying drawings illustrate implementations of the concepts conveyed in the present patent. Features of the illustrated implementations can be more readily understood by reference to the following description taken in conjunction with the accompanying drawings. Like reference numbers in the various drawings are used wherever feasible to indicate like elements. Further, the left-most numeral of each reference number conveys the Figure and associated discussion where the reference number is first introduced.

FIG. 3 shows an exemplary access policy in accordance with some implementations of the present concepts.

FIGS. 7 and 8 show exemplary entities in accordance with some implementations of the present concepts.

DETAILED DESCRIPTION

Overview

This discussion relates to providing an access control framework for a database system. For example, in some implementations, an abstraction is bound to one or more resources. Resources can be queryable, such as a view that extracts data from one or more database tables. The abstraction can include one or more rules that can be applied to those resources that are bound to the abstraction. For the purpose of this document, the abstraction is referred to as an "access policy." In some implementations, various user roles can also be defined and the rules associated with a given access policy can be user role-specific.

The disclosed implementations are described in the context of a health care scenario. As mentioned above, access control in a health care context can be a challenging problem. Consider a personal health care record for a patient. There may be many different sources of patient data used to populate a health care database, e.g., various hospitals, individual physicians, patient-supplied records, etc. Some of this data may be sensitive, e.g., a patient's status as an HIV-positive individual needs to be protected. Moreover, many different users or applications may need access to the records, such as doctors, medical billing personnel, the patients themselves, and/or applications that are used by the different users to interface with the records.

In some circumstances, many different resources may be defined to support the various users of a health care database, and the users may then query against these resources. For example, the resources can be individual views that are defined for billing records, insurance information, hospital or clinic visits, lab results, patient clinical data, etc. As the requirements for supporting the users change over time, new views may be written or existing views may be modified to support these changing requirements. As mentioned above, writing custom access conditions for each new or modified view can be challenging.

Thus, in the following discussion, an abstraction such as an access policy is associated with one or more resources. As users request data from a database, e.g., by querying on the resources, the access policy is used to ensure that the users are granted access to the data in a manner that is consistent with the appropriate access privileges. The access policy can thus provide a centralized mechanism for enforcing access constraints without the burdens associated with customized conditions for each resource.

Health Care Scenario

Figure 1:
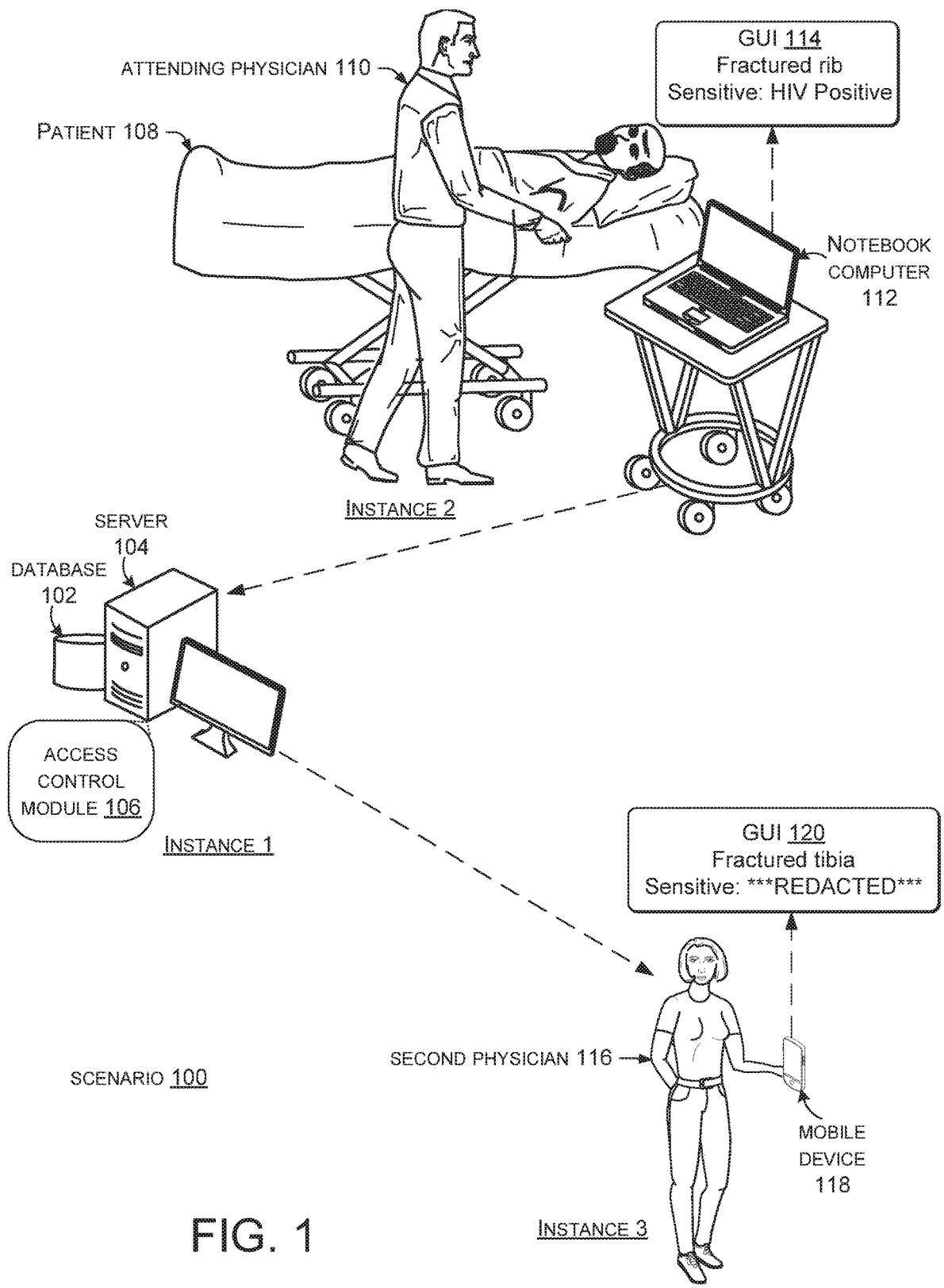
FIG. 1 shows an example scenario in which some implementations of the present concepts can be employed.

FIG. 1 illustrates a scenario 100 in which an access control framework can be employed. Scenario 100 involves instances 1-3, each of which is discussed below. Starting at instance 1, example scenario 100 involves patient data being stored in a database 102 on server 104. For example, the patient data can include personal health care records for various patients that are associated with a particular health care group, e.g., one or more hospitals, insurance companies, clinics, etc. Access control module 106 can be provided on server 104 to allow various users to access the personal health care records. As discussed in more detail below, access module 106 can do so using one or more access policies that enforce rules on one or more resources.

At instance 2, a patient 108 presents for care at an emergency room. In this example, assume that patient 108 has been admitted with an apparent rib fracture and sent to the radiology department. The patient may also be sent for one or more lab tests, e.g., x-rays, HIV test, etc. Results of the lab tests are uploaded to database 102 and the lab results are added to one or more database tables. Attending physician 110, a doctor in the radiology department, can use a client device such as notebook computer 112 to retrieve the x-ray and HIV lab results by using one or more resources to query database 102. If indicated by an access policy, access control module 106 can filter the results provided to the attending physician so that they are consistent with access privileges available to the attending physician. For example, the attending physician may be able to access all of the lab results because he is a member of the department to which the patient is admitted, e.g., the radiology department. The lab results can be provided to the attending physician via a GUI 114. GUI 114 can include various data from the patient's lab results, indicating that the patient has a fractured rib and is HIV positive.

At instance 3, a second physician 116 reviews the lab results on another client device, e.g., mobile device 118. For example, the second physician may be notified that patient 108 has a broken rib and that the attending physician would like the second physician to review the x-ray results so that the two physicians may consult about treatment options. However, the second physician may not be a member of the same department as the attending physician, and may be prohibited by state law from reviewing some of the lab results. For example, the patient's status as HIV positive may be sensitive data that the second physician is not permitted to see, e.g., in Washington state, where HIV status is considered sensitive medical data that is protected by law from being shared without patient consent.

Thus, the access control module can filter the results provided to the second physician so that the HIV status is redacted when provided to the second physician via GUI 120. Note also that, in some implementations, the second physician and the attending physician can both access the database using the same resource, e.g., both physicians may query on the same view. As discussed in more detail below, the access control module can rewrite the view executed by both physicians to provide them with different results, e.g., patient data that is consistent with their respective access privileges.

TERMINOLOGY

The following description will use certain database terminology that is described herein. For the purposes of this document, a physical or database table is an underlying table in the database where records are physically stored and updated, and is generally defined in the database schema. A database view (e.g., a SQL view) is a query that can be explicitly defined in the database schema for the database, and that extracts data from the physical tables. In some cases, a database view can be associated with metadata to create a baseview. Baseview metadata can generally be used to allow the baseview to use different column names than an underlying database view, limit the baseview to a subset of columns from the underlying database view, list users that are allowed to see the baseview, combine multiple database views, etc. Note that the term "view" as used herein includes both baseviews and database views.

Views and tables are examples of "resources," which is used herein as a general term to reflect any representation used by a user or client device to request, modify, or delete data. For example, resources can be data objects that include queries or commands that retrieve data from a database or modify the data in the database by deleting, inserting, or altering records. For example, a resource can support updates that include SQL INSERT/DELETE/UPDATE commands, or calls to stored procedures that perform the updates. In the following specific examples, baseviews are used as exemplary resources and users can query on a baseview, e.g., by selecting one or more columns from the baseview. The output of a baseview, i.e., the query results, can be affected by modifying the query based on rules so that certain users cannot access certain data. For other types of resources, e.g., resources that allow modification of the data in the database (SQL commands such as INSERT, DELETE, UPDATE), the input to the resources can be modified based on the rules so that users cannot modify certain records or columns in the database. The concepts discussed herein, however, are readily extensible to other data representations that are used as resources. For example, data structures other than relational tables, e.g., object-oriented databases or other data representations can be employed to implement the present concepts.

In the following specific examples, executing a view results in a table constructed from the physical database tables by one or more relational operations, e.g., JOIN, SELECT, etc. Note that views can be defined with respect to other views, e.g., one view can perform relational operations on one or more other views instead of, or in addition to, physical tables. In such a case, database 102 can resolve the view by "unwinding" the view until the view is expressed as references to the physical database tables.

Generally speaking, each client that accesses the data in the physical tables can do so using a view. For example, clients can write queries on views and send these queries to server 104. Note that if a client writes a query on a baseview, server 104 can execute the baseview by rewriting the baseview to refer to the database view associated with the base view and, in some instances, use the metadata for the baseview to constrain the underlying database view. For example, the baseview may specify that only certain user-accessible columns can be retrieved from the underlying baseview.

In the example shown in scenario 100, a single baseview called BV_LAB_OBR can be used to retrieve lab observations from one or more physical database tables in the database. Thus, this baseview is executed twice in the scenario, e.g., once to provide data to the attending physician at instance 2, and again to provide data to the second physician at instance 3. As discussed in more detail below, the access control module can rewrite the BV_LAB_ORB baseview when the baseview is executed so the results are consistent with one or more access policies.

A SQL DOM (structured query language domain object model) is a tree that describes the construction of a query from one or more views or tables. A SQL DOM can include one or more classes that load a particular query by parsing a SQL statement. A SQL DOM can be used to rewrite a SQL statement to include one or more filter conditions, as set forth in more detail below. Note, however, that other suitable programming languages can also be used to implement the techniques disclosed herein. For instance, some of the concepts described herein (e.g., manipulating a SQL DOM)

can be implemented in application code via languages such the Java® or C#® programming languages, using the NET® framework, etc.

For the purposes of example, two baseviews are discussed—BV_LAB_OBR and BV_CLINICAL, having the following schema:

BV_LAB_OBR: (EID, ObservationDtTm, Technician, XRayResults, HIVLabResults)

BV_Clinical: (EID, FName, LName, AttendingPhysician, Department, AdmitTime, DischargeTime)

Thus, BV_LAB_OBR and BV_Clinical are baseviews that may correspond to one or more database views that retrieve data from the physical database tables in the database. The baseviews can be defined by an administrator of the database for use by various database client devices, such as notebook computer 112 and/or mobile device 118. The client devices can retrieve data from the database by writing queries on the baseviews to gather information of interest for users such as the physicians.

First Method Example

Figure 2:
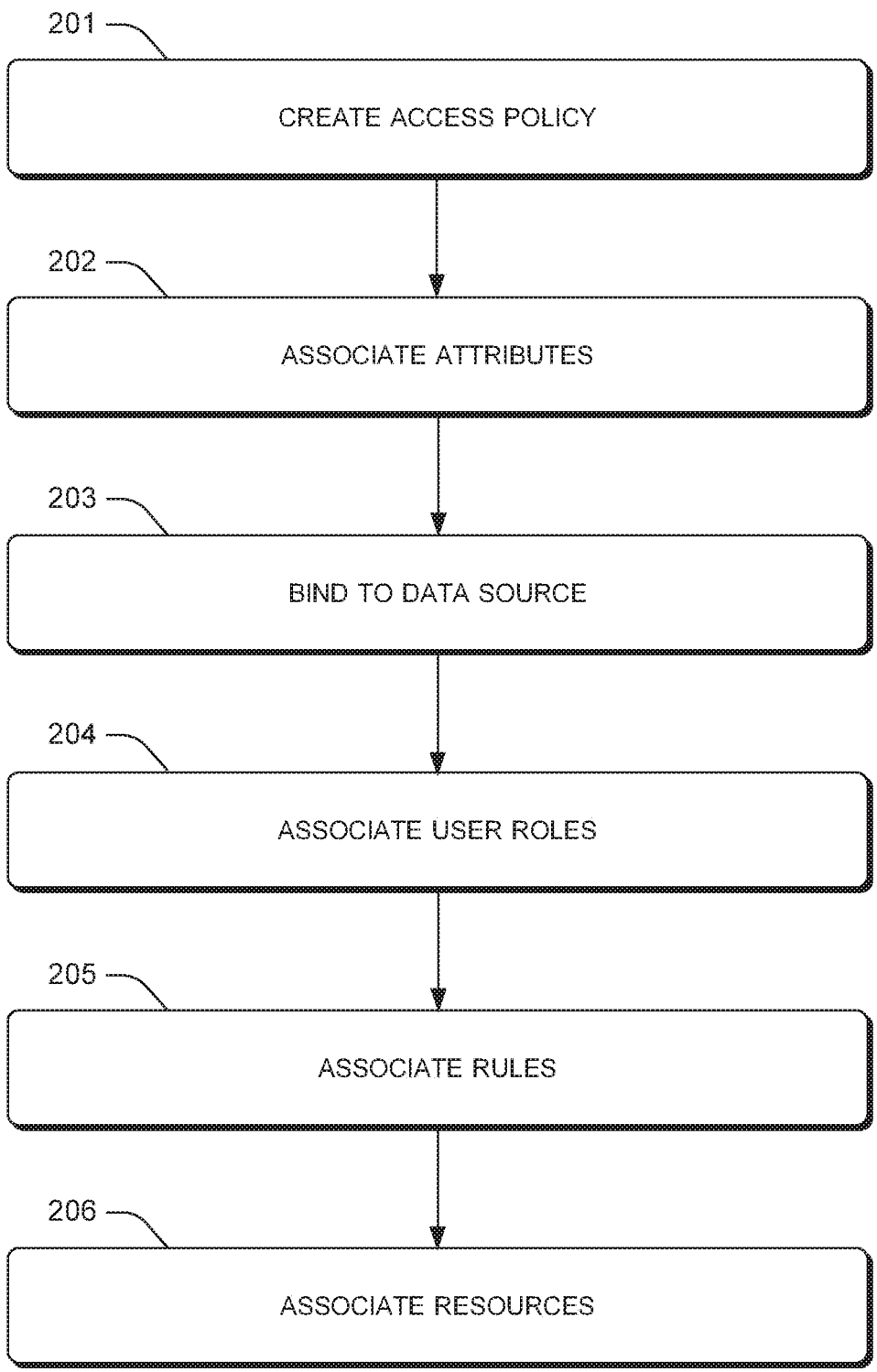
FIGS. 2, 4-6, and 9 show examples of flowcharts of methods in accordance with some implementations of the present concepts.

FIG. 2 illustrates an exemplary method 200 that can be used to bind a resource such as a view to an access policy. Generally speaking, the discussion associated below with respect to method 200 can be performed at design time, e.g., before the access policy is applied to inputs or outputs of one or more resources. For simplicity of exposition, the following example is discussed with respect to a single access policy that is bound to a single view. However, as discussed in more detail below, method 200 can be applied for any number of resources and for any number of access policies.

At block 201, an access policy is created. For example, an administrator of database 102 may create a VISIT access policy associated with patient visits to a hospital. The administrator may wish to use the access policy to control access to data that is associated with various patient visits.

Next, at block 202, attributes are associated with the access policy. For example, the administrator may define numerous data attributes that are associated with the access policy, including a primary key. In the case of the VISIT access policy, the primary key may be EID. EID may be an identifier of an individual patient visit to the hospital. The access policy can also be associated with additional attributes, e.g., a Department attribute that identifies the hospital department where the individual patient visit took place, e.g., radiology, cardiology, etc.

Next, at block 203, the access policy can be bound to a data source. For example, the VISIT access policy can be bound to a database table that includes columns corresponding to the attributes. Thus, each of the columns from the data source (e.g., table) can be mapped to an attribute of the access policy. As discussed more below, when a user accesses a resource, the value of the individual columns that are bound to the access policy attributes can be used as the values of the attributes. The values of the attributes can be applied by various rules to change the input or output of the resource.

Next, at block 204, one or more user roles can be associated with the access policy. For example, the user role can be relatively general, e.g., clinical personnel (doctors, nurses, physicians) or more specific, e.g., doctors in a particular department. Thus, each user role can identify a group of users by one or more attributes that the users have in common.

Next, at block 205, one or more rules can be associated with the access policy. Rules can be assigned to individual user roles. Moreover, the rules can be applied to the data sources that are bound to the access policy. For example, a database administrator can write rules on the VISIT access policy that they wish to apply each time a user with one of the user roles attempts to access the database. As discussed in more detail below, the administrator can express these rules using the attributes of the access policy.

Next, at block 206, one or more resources, such as views, stored queries, tables, etc., can be associated with the access policy. For example, the BV_LAB_OBR view may be associated with the VISIT access policy by the database administrator. Once the database administrator establishes this binding, future queries that reference the BV_LAB_OBR view may have rules applied to those queries. Generally, the rules are applied to the access policy attributes, which in turn can be obtained from a "default" data table. In some instances, a particular attribute of the access policy can be bound to a particular column of a resource that is bound to that access policy. This can cause the access control module to override the binding of that attribute so the attribute value is obtained from the bound resource instead of the default data source. This is discussed in more detail below.

For example, the EID attribute of the VISIT access policy can be bound to the EID attribute of the BV_LAB_OBR view. At runtime, the value of this attribute will be taken from the BV_LAB_OBR view instead of the default data source when the BV_LAB_OBR view is accessed by a user, while the other attributes will still be taken from the default data source. However, when other resources are accessed, the value of the EID attribute will still be taken from the default data source. From the perspective of a database administrator that is writing a rule, the rule can be expressed using the access policy attributes regardless of whether a particular attribute value is obtained from the default data source or overridden so that the attribute is obtained from a resource column.

A concrete example of applying method 200 is explained as follows to create access policy 300, shown in FIG. 3. In this example, the database includes a table (or view) called VisitInfo that includes columns such as (VisitID, AdmitDate, AdmitDepartment, State) where VisitID identifies individual visits, AdmitDate identifies a time of when the patient was admitted, AdmitDepartment that identifies the department to which the patient was admitted, and State identifies the state where the visit took place. The database includes a second table or view called InsuranceInfo that includes an InsCo column that identifies a patient's health insurance company. As shown in FIG. 3, the EID primary key of the VISIT access policy can be bound to the VisitID column of the VisitInfo table, the Department attribute of the VISIT access policy can be bound to the AdmitDepartment column of the VisitInfo table, the State attribute can be bound to the State column of the VisitInfo table, and the Insurance attribute can be bound to the InsCo attribute of the InsuranceInfo table.

As explained in more detail below, the rules associated with the VISIT access policy at block 205 can be applied as users provide queries that reference the bound resource, e.g., the BV_LAB_OBR view. Each visit has a unique VisitID in the VisitInfo table that identifies the row where the data for that visit is stored. Thus, when the BV_LAB_OBR view is executed, the rows in the database can be filtered based on the rules so that only the appropriate rows are retrieved. In other words, fewer rows of data may be returned than are requested by the view or a query written on the view.

For the purposes of example, the database administrator can define a user role for doctors in the radiology department. This rule can allow doctors in the radiology department to view visit information any time a patient visits the radiology department. The rule can be written as an expression "Rule1=[VISIT].[DEPARTMENT]='Radiology'." As explained in more detail below, this rule can be applied when a request (e.g., the BV_LAB_OBR view) is received and applied to ensure that doctors in the radiology department can access the visit info for this department.

The above example shows how an access policy rule can be defined for filtering individual records of a data source, e.g., rows of a database. In some implementations, access policy rules can also be defined that have the effect of restricting access to individual fields such as columns of a database. As discussed in more detail below, Rule1 can allow doctors in the radiology department to view sensitive information for patients who visit this department. In contrast, Rule2 can allow doctors in Washington to view visit information for visits in the state of Washington, but not sensitive information for the patients. This can be accomplished by providing rules that specify which user roles can access data that is labeled as sensitive.

Second Method Example

Figure 4:
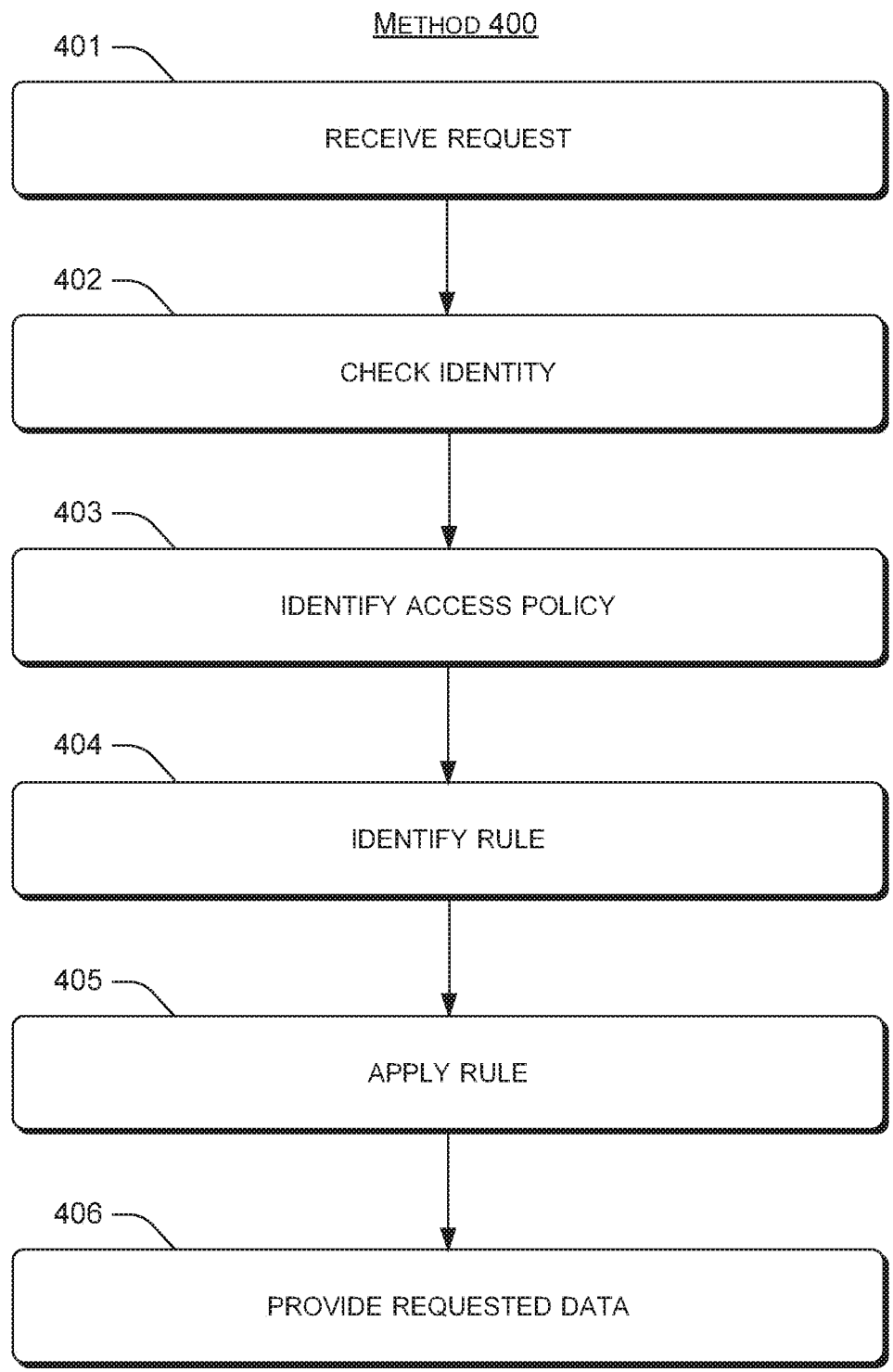

FIG. 4 illustrates an exemplary method 400 that can be used to apply an access policy to a received request for data. Generally speaking, the discussion associated below with respect to method 400 can be performed at run time, e.g., when users request or execute one or more resources such as views or stored procedures. For simplicity of exposition, the following example is discussed with respect to a simple query on a single baseview (BV_LAB_OBR) that is bound to a single access policy (VISIT). However, as discussed in more detail below, method 400 can be applied for any number of views and for any number of access policies.

At block 401, a request for data is received from a user. For example, a user can execute a query that retrieves one or more columns from a view. In the example that follows, the query retrieves all of the columns of the BV_LAB_OBR view, e.g., the query can be "SELECT BV_LAB_OBR.*FROM BV_LAB_OBR."

Next, at block 402, an identity of the client that is requesting the data can be checked. For example, users may have associated log-ins (usernames, passwords, etc.) that are submitted to server 104. Each login may be associated with one or more user roles, e.g., a doctor's log-in may be sufficient to identify the doctor as a member of a particular department, a doctor in a particular state, etc. In some instances, the various user roles of different individuals are maintained in database 102, e.g., in one or more tables.

Next, at block 403, one or more access policies can be identified. In the example introduced above, the BV_LAB_OBR view was bound to the VISIT access policy. Since the query received at block 401 references this view, the VISIT access policy is identified as an access policy that is applied to this request.

Next, at block 404, individual rules in the access policy can be identified. As mentioned above, rules can be included in an access policy that specify how individuals with particular user roles can access the data in the database. Continuing with the example, individuals with the user role of doctors in the radiology department are permitted by a rule to view visit information for visits to the radiology department, and this rule can be identified at this time. More generally, each time a user requests access to a resource, each of the user's roles can be identified so that rules for each of the user's roles can be applied. The attributes of the access policy can be taken from the default data source to apply the rules. However, as mentioned above, if a given attribute has been bound to a column of the resource being accessed, the default data source is overridden for this attribute and the attribute is instead taken from the column of the resource.

Next, at block 405, the rule can be applied. Generally, applying a rule can include using the values of the access policy attributes to modify or limit the inputs or outputs of a resource. In this example, the received query references a baseview, so the rule is applied to limit the outputs of the baseview using the attributes. For example, the database may have many different visits reflected in the VisitInfo table, and not all of these visits are necessarily to the radiology department. However, the received query "SELECT BV_LAB_OBR.*FROM BV_LAB_OBR" does not distinguish between different departments. Thus, in some implementations, the received query can be rewritten to filter the results so that only visits to the radiology department are retrieved. Query rewriting is discussed in more detail below.

Also, note that when a user accesses a resource to modify or delete data in the database, inputs to the resource can also be modified based on a rule. For example, users in the radiology department may be prevented by a rule from deleting records for patients that are not in the radiology department. In such instances, the inputs to a SQL "DELETE" statement can be modified by rule so that the DELETE statement does not affect records for other departments.

Next, at block 406, results can be provided to the user. For example, the data retrieved by the rewritten query can be provided to the doctor that sent the data request at block 401. In some implementations, only results that are not prohibited by the identified rules are provided, and other requested data is not provided (e.g., prohibited columns or rows).

Using methods 200 and 400 as set forth above, an access policy can serve as a centralized abstraction for access control to data. As mentioned above, multiple resources (e.g., views) can be associated with a single access policy. In the example of FIG. 3, another baseview, BV_CLINICAL, is also associated with the VISIT access policy so that the Rule1 and Rule2 will also be applied to queries on BV_CLINICAL.

Thus, the views themselves do not need to be manually rewritten to apply access control rules on a view-by-view basis. Rather, by maintaining the rules in an access policy and associating the views with the access policy, the rules can be applied to all of the views, e.g., by dynamically rewriting views or queries that reference the views as they are received. This can be beneficial, e.g., for a database administrator who wishes to apply a common set of rules to a number of different views. Moreover, as mentioned above, the individual rules can be organized on a user role-by-user role basis so that different rules can be applied to users having different user roles. Additional examples of access policies and how rules and user roles can be applied in a health care context are discussed below.

Note also that the access control module can be provided as a database management application that performs methods 200 and 400. From the perspective of a customer (e.g., database administrator) that uses the access control module on their database system, the processing described above may be transparent, e.g., the database administrator does not need to know about the query rewrites, etc. Moreover, the access control module can perform this processing independently of the underlying database schema (physical tables and database views) and/or baseviews used by the customer.

Data Sources and Query Rewriting

As mentioned above, an access policy can be bound to various data tables, e.g., that include columns corresponding to the attributes of the access policy. However, when applying an access policy as discussed above with respect to method 400, it can be cumbersome to access all of the various data sources (tables or views) that are referenced by the baseview, particularly where the columns are spread across a large number of other views or tables.

It can be more efficient to maintain a centralized default data source that includes the particular columns that are bound to the attributes of the access policy. In other words, data from several different tables can be combined into a single table that serves as a default data source for the access policy. The other tables can still be used for other purposes, but the access policy can be applied using the default data source instead of the other tables. The access policy can be bound to this default data source, e.g., at block 203 of method 200. In some implementations, each attribute of a given access policy can have a corresponding column in the default data source for that access policy. Moreover, the primary key attribute of the access policy serves as the primary key of the default data source table. As mentioned above, individual attributes of the access policy can be overridden so that they are taken from a column of a resource instead of the default data source when that particular resource is accessed.

One way to apply an access rule is to rewrite a received query to perform a JOIN operation on the tables that are bound to the access policy. If a default data source is not used and an access policy is bound to multiple tables, this can result in more complicated rewritten queries, because more than one table may need to be joined, depending, e.g., on which tables need to be included for the attributes of the access policy. By using a default data source table, the JOIN operation only needs to be performed on the default data source table itself, rather than the various other tables or views from which the default data source is maintained.

Considering the previous example, let the default data source table be named "PV1." The query received in the example above can be rewritten as:

```
SELECT BV_LAB_OBR.* FROM BV_LAB_OBR
LEFT JOIN PV1 ON BV_LAB_OBR.EID=PV1.EID
WHERE PV1.DEPARTMENT='Radiology'
```

The underlined portions of the rewritten query can be used to apply the rule. Note, for example, that the WHERE condition in the rewritten query means that only the visits to the Radiology department will be retrieved and provided in response to the query. This is the case even though the original received query, SELECT BV_LAB_OBR.*FROM BV_LAB_OBR, does not include any conditions and thus, without being rewritten, could have retrieved data for visits to other departments. Viewed another way, the default data source contains the columns used to apply the rules for the access policy. Thus, even if the received query or view does not retrieve the columns used by the rule, the column can be used for security purposes by doing the JOIN with the default data source.

Note that in the example above, the BV_LAB_OBR view may not retrieve the Department column from, e.g., the VisitInfo table. The solution presented above is to JOIN the BV_LAB_OBR view with the default data source PV1 so that the condition on the Department column can be applied. However, in some cases, a view may retrieve a column that is used as a condition for a rule that is being applied by the access policy. In such a case, the rule can be applied without doing a JOIN operation on the default data source.

For example, consider the baseview BV_CLINICAL, which can retrieve data from the Department column. Now, if a user executes a query on the BV_CLINICAL view, e.g., "SELECT*FROM BV_CLINICAL," the query can be rewritten as follows:

```
SELECT * FROM BV_CLINICAL
WHERE BV_CLINICAL.DEPARTMENT='Radiology'
```

Here, the underlined portions of the rewritten query are used to apply the rule as mentioned above. In this case, however, the query can be rewritten without performing a JOIN on the default data source because the Department column is already retrieved by the BV_CLINICAL baseview.

The above description shows how query rewriting can be performed to implement rules that filter individual records from a data source. However, as mentioned above, some rules may filter on a field (e.g., column of a database). For example, if a rule specifies that a user cannot retrieve a sensitive column that is retrieved by the BV_CLINICAL baseview, queries referencing this view can be rewritten so that the sensitive column is not retrieved or is redacted before being provided to the user. More detailed examples are set forth below.

Additional Examples

Access policies can be created to represent a real-world concept, e.g., a visit to a hospital. In a health care context, other examples of access policies could include patients, billing accounts, etc. For example, a patient access policy could be defined with a rule that only allows patient data to be retrieved by the doctor that is the attending physician. Similarly, a rule for billing accounts could only allow billing information to be retrieved by billing personnel at a hospital, and could prevent other individuals from retrieving the billing information.

The rules applied by a given access policy can depend on various factors, e.g., hospital policies, geographic location, privacy laws, etc. In some cases, data may be available to all doctors in a hospital for a limited time (e.g., 72 hours) after a patient visits the hospital. This rule can be implemented by a WHERE condition that specifies that the visit discharge time is no more than 72 hours prior to the time when the request is received. Note that this can be implemented by adding a discharge time attribute to the access policy and to the default data source table, if one is used. This rule can be applied in the same access policy with rules such as the previously introduced radiology example or, more generally, doctors in the department to which the patient is admitted may be able to view the visit information indefinitely, even after the 72-hour period has expired.

Third Method Example

As discussed above with respect to methods 200 and 400, using access policies as disclosed herein can provide access control to various data sources by filtering the records in the data source. In particular, the examples shown above use rules to filter which rows of one or more database tables are available to a client device or user. As also mentioned above, it can be desirable to filter which fields from a data source are available to client device or user. In other words, a user or client device may be able to access a particular record, but not necessarily access all of the fields for that record. In a health care context, this may mean a doctor can access data regarding a patient visit, but is prohibited from viewing certain sensitive data such as the patient's HIV status. In implementations where the data source includes one or more database tables, this can be accomplished by limiting access to one or more sensitive columns of a database table.

One difficulty that can be presented in such circumstances is that some queries may inadvertently reveal sensitive data. For example, consider a query that retrieves only one column from the database, PatientName. However, the query is written with a condition to only retrieve records where "HIVStatus=Positive." Even though this query does not return the HIVStatus column, the user will clearly be able to be able to tell which patients have HIV by executing such a query, since the results will only be patients with HIV positive status. Thus, it is not always sufficient to prevent users from retrieving sensitive fields from a data source. Rather, conditions specified by the user in querying the data source can also inadvertently reveal sensitive data.

Figure 5:
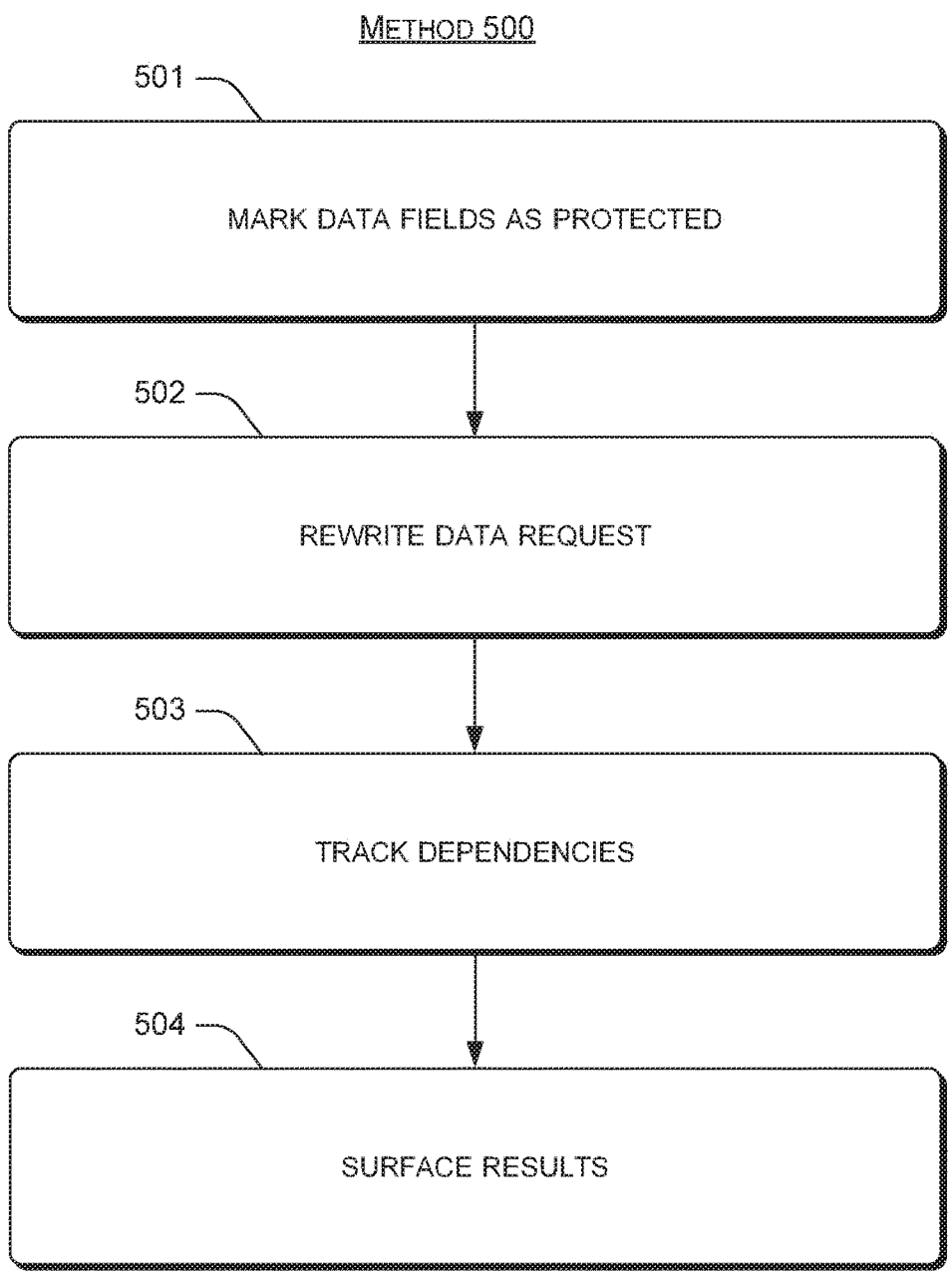

FIG. 5 illustrates an exemplary method 500 that can be used to implement access rules on protected data fields such as sensitive data fields or auditable data fields. Sensitive data fields are columns that are labeled as sensitive, and, as mentioned above, rules can be defined so that only particular user roles have access to sensitive columns. Auditable data fields are fields whose values are recorded for any user that accesses them. They go into an audit log that identifies the fields and records that are accessed, as well as the users that accessed them. The audit log can be reviewed by the database administrator to determine if there has been any improper data access.

The following example is discussed with respect to two user roles, two rules, and one view. The view name continues from the previous example, e.g., BV_LAB_OBR. The user roles are doctors in radiology, and doctors in the state of WA. Rule1 says that doctors in radiology can see lab results, including sensitive fields (e.g., UNLOCK sensitive in FIG. 3), from columns such as HIV status for any patients in the radiology department. Rule2 says that doctors in the state of Washington can see lab results for patients in Washington, but cannot see the sensitive fields (e.g., LOCK sensitive in FIG. 3) unless authorized by some other user role, e.g., being in the radiology department. These rules can be created, e.g., using method 200 as discussed above.

At block 501, data fields are marked as protected, e.g., sensitive and/or auditable. In the case of a database table, the access policy can associate a sensitive label with a particular column of the table. In this example, the HIVLabResults column retrieved by the BV_LAB_OBR view is marked as sensitive.

Next, at block 502, a data request is rewritten to include conditions for the sensitive or auditable column. For example, if a user has submitted a query "SELECT [BV_LAB_ORB].*" then this query can be rewritten with conditions based on rules for the sensitive data fields. In the following example, a condition called "GR0" is added to the query to reflect whether the first rule applies, e.g., whether the requester is a doctor in the radiology department. Another condition called "GR1" is added to the query to reflect whether the second rule applies, e.g., whether the requester is a doctor in the state of Washington.

Next, at block 503, dependencies are tracked using the conditions in the rewritten data request. In this example, the rewritten query "SELECT [BV_LAB_ORB].*" can be executed using different CASE statements to populate each condition. The values of the conditions GR0 and GR1 can be applied in separate CASE statements that determine whether the sensitive column is redacted by the rewritten query.

Next, at block 504, results are surfaced consistently with the rules. In this example, for a doctor in the state of Washington that is not in the radiology department, the HIVLabResults column returned by the BV_LAB_ORB view may have a value of "*REDACTED*" displayed on the doctor's computer. For another doctor in the radiology department, this column may have a value of "HIV Positive" displayed on the doctor's computer. This is illustrated in scenario 100 of FIG. 1.

In the example provided above, the query "SELECT [BV_LAB_ORB].*" can be rewritten as follows (referred to below as "INNER QUERY #1):

```
SELECT [BV_LAB_ORB].*,
CASE WHEN PV1.DEPARTMENT='Radiology' THEN 1 ELSE 0 END
   GR0
CASE WHEN PV1.STATE > 'WA' THEN 1 ELSE 0 END GR1
FROM [BV_LAB_ORB] LEFT JOIN PV1 ON
BV_LAB_OBR.EID=PV1.EID
WHERE PV1.DEPARTMENT='Radiology' OR PV1.STATE > 'WA'
```

Moreover, the following logic can be applied to mask the sensitive columns based on GR0 and GR1, respectively, using an outer layer query on top of INNER QUERY #1:

```
SELECT CASE WHEN GR0=1 THEN [SENSITIVE COLUMN] ELSE
   '*REDACTED*' END AS [SENSITIVE COLUMN] FROM
   [INNER QUERY #1]
```

As shown above, a query can be rewritten to include conditions that are populated when the query is executed. These conditions can affect whether sensitive columns are returned to the user or are instead redacted.

Furthermore, in some implementations, queries can be rewritten so that values of sensitive columns are not revealed even when the query does not actually retrieve the sensitive columns, but merely uses the sensitive columns in conditions to retrieve other columns that are not sensitive. For auditable columns, queries can be rewritten so that the auditable columns are surfaced even when the queries do not actually retrieve the auditable columns. Thus, if a user executes a query that is dependent on an auditable column but does not retrieve the auditable column, the audit log will still reflect that the auditable columns were accessed by the user.

Application Roles

Generally speaking, the techniques described above relate to access control on data, e.g., on a record-by record (row) or field-by-field (column) basis. In some implementations, access control can also be performed on functionality, e.g., application functions, or application data that is accessible via application views. Note that the term "function" as used herein includes other similar terms, method, routine, etc. as they used in application development contexts. For example, an application may provide 10 functions that can be called, e.g., the application interface exports these 10 functions with function definitions (function names, input arguments, output arguments, etc.). Some of these functions may be restricted to use by a first group of users (e.g., a user role), and other functions may be restricted to use by a second group of users (e.g., a different user role). The application may also provide various data values that can be read and/or modified by users of the application. Users can obtain these values by one or more application views provided by the application. Each application view can provide a different subset of application data to users. Thus, it may be desirable for some users to be provided with access to certain application views but not other application views.

The following example can arise in a health care context. Consider two user roles for doctors that both use a particular application. Doctors having a user role that permits prescribing medications may need to execute individual functions that create prescriptions. Other doctors may be responsible for reviewing prescriptions of the prescribing doctors, and thus may have a different user role. The application may include a number of different functions that can be called. Some of these functions, e.g., CreatePrescription( ) may be used by the prescribing doctors, and other functions, e.g., GetPrescription( ) may be used by the reviewing doctors. Moreover, it may be useful to prevent the prescribing doctors from reviewing prescriptions for other doctors, and to prevent the reviewing doctors from creating prescriptions. As set forth below, this can be accomplished using one or more application roles that each are mapped to some of the functions provided by the application.

Figure 6:
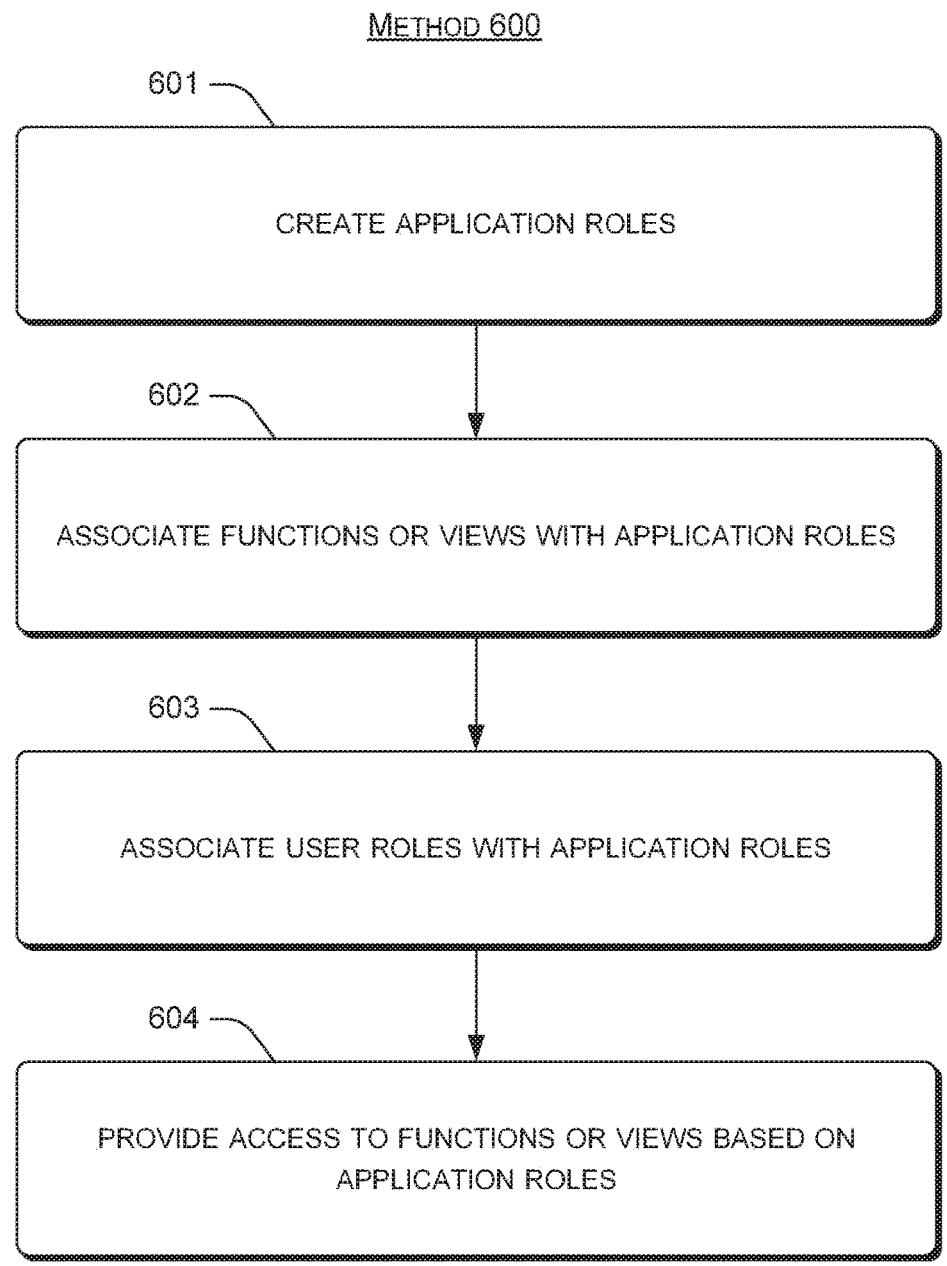

FIG. 6 illustrates an exemplary method that can be used to apply application roles for access control to application functions. The method explanation continues with the example set forth above.

At block 601, an application role is created. For example, application developers may create application roles for their applications at design time, or the application roles can be created later, e.g., via configuration files, etc. Each application role can correspond to a real-world concept such as prescribing medications, reviewing prescriptions, etc. In this example, the application roles include a PrescriptionGenerating application role and a PrescriptionMonitoring application role. In some implementations, a configuration file such as an XML file is provided at design time for use with an application. The configuration file defines the application roles and enumerates resources that are provided by the application (e.g., application data views and/or functions).

Next, at block 602, sets of application functions or sets of application views are associated with individual application roles. For example, for the PrescriptionGenerating application role, an individual application function called CreatePrescription( ) and another individual application function called RenewPrescription( ) can be associated with this application role. For the PrescriptionMonitoring application role, two other functions, GetPrescription( ) and GetPrescriptionRenewals( ) can be defined. Thus, each application role groups together various functions that are associated with that application role, e.g., functions related to prescription monitoring are associated with the PrescriptionMonitoring application role and functions related to generating prescriptions are associated with the PrescriptionGenerating application role. The association between application functions or application views and the application roles can be represented in the configuration file at design time, e.g., the system administrator can declare the application roles that are associated with each application function or application data view. Also, note that multiple application functions and multiple application data views can be concurrently associated with an individual application role.

Next, at block 603, user roles can be associated with the application roles. In this instance, the PrescriptionGenerating application role can be associated with a user role called "attending physicians," which includes all physicians in a hospital that are the attending physician for at least one patient. The reviewing prescriptions application role can be associated with a user role called "supervisory physicians," which includes all physicians in the hospital that supervise at least one other physician. For example, at runtime, after the application is deployed (e.g., installed on server 104 and accessible via notebook computer 112 or mobile device 118), the system administrator can associate various user roles with the application roles provided by the application.

Next, at block 604, the individual application functions or application views can be executed based on the application roles. For example, those users having user roles that are associated with particular application roles can be permitted to execute functions or application views for those particular application roles. Thus, the system administrator does not necessarily need to know each of the application functions or application views provided by the application. Rather, the system administrator merely needs to know that the application provides certain application roles. By associating the user roles with the application roles, access control to the application functions or application views can be implemented without requiring the system administrator to specify the individual functions or views directly.

Thus, a doctor having the "attending physicians" role but not the "supervisory physicians" role could execute the functions (or application views) associated with the attending physicians role, e.g., CreatePrescription( ) and RenewPrescription( ). This doctor, however, may not be able to execute the GetPrescription( ) and/or the GetPrescriptionRenewals( ) functions, since this doctor does not have the "supervisory physicians" role. Note, however, that in some hospitals, doctors may be both attending physicians and supervisory physicians, and thus may be able to execute all four of the functions mentioned in this example, e.g., because they are associated with user roles that cover all four functions via the two different application roles.

Method 600 can be applied in various contexts. For example, method 600 can be performed when an application is first deployed, so that the application provides method-by-method security at deployment time. In some implementations, method 600 can also be performed as the application is updated over time, and/or as resources are added to the database. As one example, a new method, CancelPrescription( ), can be added by application developers and mapped to an existing application role, e.g., the prescribing physicians role. Because the application role is already configured and access control for individual users (e.g., by user role) has already been implemented, it is possible to simply associate the new method with an application role to provide the access control for the method. Nevertheless, note that blocks 601-603 of method 600 can also be performed after design time, e.g., once the application is deployed.

More generally, application roles can be applied across more than one application. For example, the previously-introduced application with the PrescriptionGenerating and PrescriptionMonitoring roles may be called Prescriptions, and, as mentioned, provides some functions for prescribing medications and other functions for reviewing existing prescriptions. Now, another application called PhysicianTraining may schedule training sessions for physicians based on what type of practice each physician has. The developers for the PhysicianTraining application may use some existing application roles from the Prescriptions application in the PhysicianTraining application.

For example, the PhysicianTraining application may have a function called SchedulePrescriptionTraining( ) that automatically schedules mandatory training for how prescriptions must be formatted by doctors that actively prescribe medications in that particular hospital, e.g., the hospital may specify that prescriptions must be written in a particular order (BrandName, GenericName, Dosage, NumRefills). This function can also be associated with the Prescription-Generating application role. As another example, the PhysicianTraining application can also include a function called ContraindicationsTraining( ) that schedules training for physicians about contraindications for various medications. This function can be associated with both the PrescriptionGenerating and PrescriptionMonitoring application roles. Note that additional user roles can also be associated with an individual application role, e.g., a new user role called "medical board officials" could be added to allow certain medical board officials to review prescriptions.

To recap, a logical representation of the above relationships follows:

---

PrescriptionGenerating Application Role (attending physicians and state oversight officials user roles)
    Prescriptions Application
        CreatePrescription( )
        RenewPrescription( )
        CancelPrescription( )
    PhysicianTraining Application
        SchedulePrescriptionTraining( )
        ContraindicationsTraining( )
PrescriptionMonitoring Application Role (supervisory physicians user role)
    Prescriptions Application
        GetPrescription( )
        GetPrescriptionRenewals( )
    PhysicianTraining Application
        ContraindicationsTraining( )

---

Thus, both supervisory physicians and attending physicians can be scheduled for the contraindications training. This can be useful because the attending physicians may need to know about contraindications to prescribe medications effectively, while the supervisory physicians may need this training to effectively review prescriptions to ensure medications are not being prescribed without regard to contraindications. However, the supervisory physicians that are not also attending physicians may have no reason to take the training for writing prescriptions, because they may not actually be responsible for doing so.

Entity-Based Access Control

In the previous examples, an access policy was bound to a resource such as one or more views, e.g., at block 206 of method 200. As also discussed, users can provide queries that are written against views, and the access policy can be applied to enforce individual rules on these queries. In some circumstances, it may be useful to bind an access policy to multiple resources or parts of a resource (e.g., not all of the columns of a view or table). Furthermore, it may be useful to provide a construct so that access rules can be inherited where appropriate.

The following discussion relates to a construct called an "entity." For the purposes of this document, an entity is a collection of data, e.g., an object or other data structure that a user can access directly or query against. An entity can be associated with multiple resources such as views. For example, an entity representing a patient can be created that includes attributes taken from several different database views or tables. The patient entity can include a number of rules that apply to these attributes. Thus, from one perspective, the entity can be considered as including an access policy. Because the access policy and individual rules are associated with the entity, another entity representing individual patient visits can be created that inherits these rules from the patient entity. Thus, from the perspective of a database administrator, rules defined on the patient entity are automatically applied to the visit entity. For example, if the database administrator adds a new rule to the patient entity, this rule could also be applied to the visit entity by inheritance. Note, however, that in some implementations, a first entity does not necessarily inherit attributes from a second entity even though the first entity inherits rules from the second entity.

More generally, an entity can be thought of as a refinement or expansion of the baseview concept described in the previous implementations. Like a baseview or other types of resources, entities can also be queryable, i.e., users can request data using queries on the entities that specify what data is being requested. Using entities, individual columns from multiple database views can be pulled together to represent one concept, e.g., patients, visits, etc. Thus, for example, a user query such as SELECT * FROM Patient, Visit can obtain columns from both the Patient and Visit entities, apply access rules for both the patient and visit entities to the query, and provide the user with a response that is appropriate given the access rules defined in these entities. Also, as discussed more below, individual rules can be inherited from the Patient entity to the Visit entity so that a query against just the Visit entity also automatically applies the rules that are inherited from the Patient entity.

Figure 9:
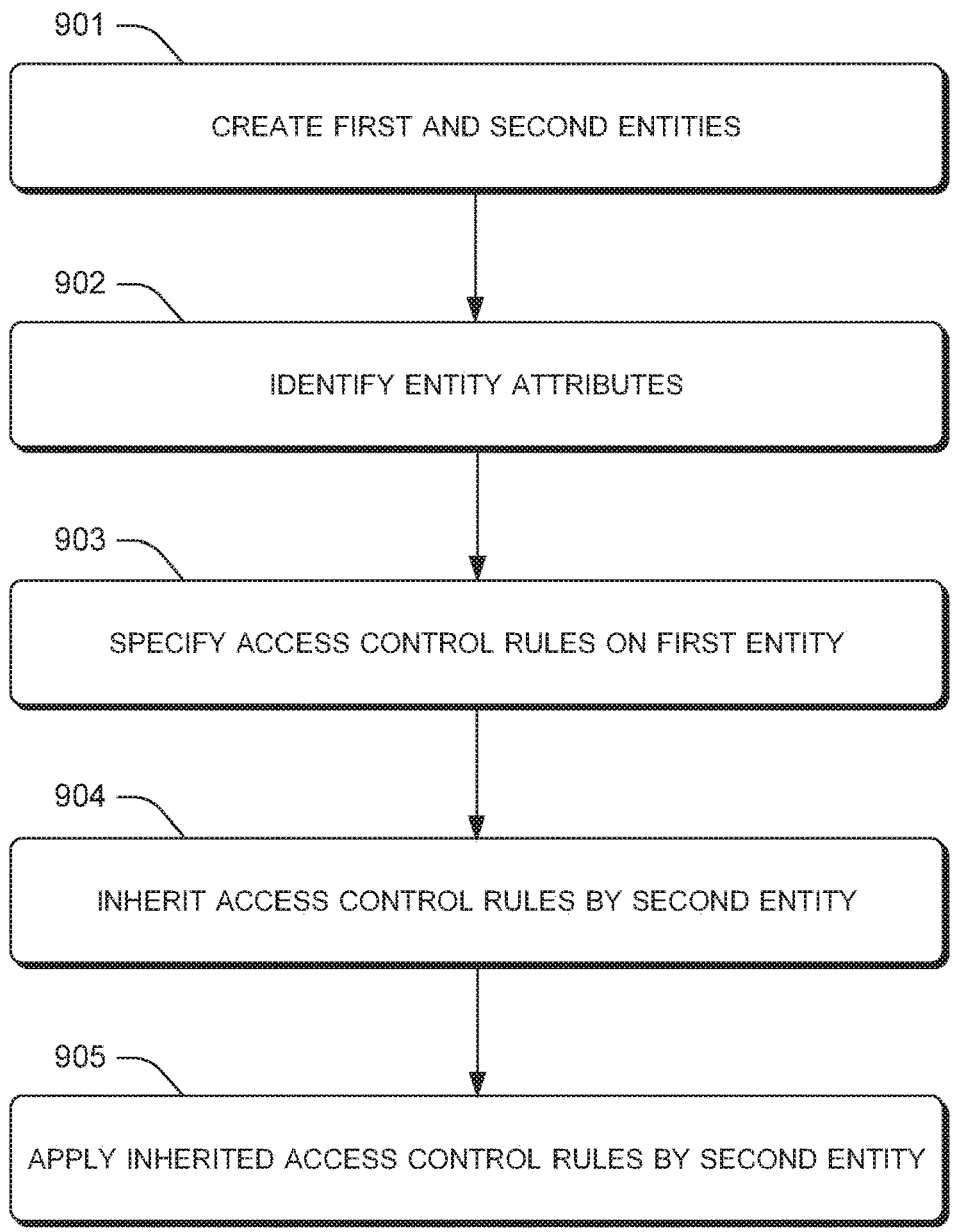

The following discussion refers to FIGS. 7-9. FIG. 7 illustrates a Patient entity 700, FIG. 8 illustrates a VISIT entity 800, and FIG. 9 illustrates an exemplary method 900 that can be used to apply entities for access control. The method explanation continues with the example set forth above.

At block 901, a first entity and a second entity are created. For example, the PATIENT Entity can be created and intended for users to query against for patient data. Generally speaking, the PATIENT entity can provide data related to individual patients that are also shown as attributes of the Patient entity, e.g., name, address, etc. Similarly, the VISIT entity can be created that is intended for users to query against for data related to individual visits to a health care facility, shown as attributes of the VISIT entity.

At block 902, entity attributes are identified for the first entity and/or second entity. For example, individual attributes can be defined in a similar manner as discussed above for access policies. In some implementations, a primary key is also defined at block 902 by selecting an individual attribute to be the primary key.

At block 903, access control rules are specified on the first entity. For example, the database administrator may specify rules similar to those set forth above, e.g., on a role-by-role basis.

At block 904, access control rules are inherited by the second entity. For example, the database administrator can choose to have the second entity, e.g., the VISIT entity, inherit the access control rules from the patient entity. This inheritance can be established, e.g., by associating an attribute of the VISIT entity with an attribute of the PATIENT entity.

At block 905, the inherited access control rules are applied by the second entity. For example, a query on the second entity such as "SELECT * FROM VISIT" can be rewritten as:

```
SELECT * FROM VISIT LEFT JOIN PATIENT ON
VISIT.OID=PATIENT.OID
WHERE [PATIENT].[IsVip]='FALSE' OR PATIENT.OID IS NULL
```

This rewritten query illustrates a rule that can be inherited by the visit entity from the patient entity. In this example, OID is a patient ID that uniquely identifies patients. The rule can have two parts, a first part (PATIENT.ISVIP='FALSE') and a second part (PATIENT.OID IS NULL). The first part of the rule prevents users from seeing data for patients who are VIPs "very important persons."

The second part of the rule is used for instances where the VISIT table has records with OID values that do not match any OID values in the PATIENT table. This is particularly useful in instances where data integrity is imperfect, e.g., as is often the case in the health care industry. For example, a patient may visit a clinic and an instance of a visit can be created, but the patient may not have an OID that is created at this time. Thus, there is a valid visit record, but no record for the patient. The second part of this rule indicates that, in this situation, the VIP rule is not enforced on the visit because there is no corresponding patient. Access is allowed by this rule under such circumstances. Note that the second rule does not appear in FIG. 7, and does not need to be provided by an administrator. Rather, the second part of the rule can be generated automatically as part of block 905.

Furthermore, note that a user querying on the PATIENT entity can obtain columns from multiple views or tables. The binding between an entity and a view or table can be established via a "binding query." Once an entity is associated with a binding query, queries executed against the entity are in turn executed by the binding query, subject to any rules associated with the entity.

System Example

Figure 10:
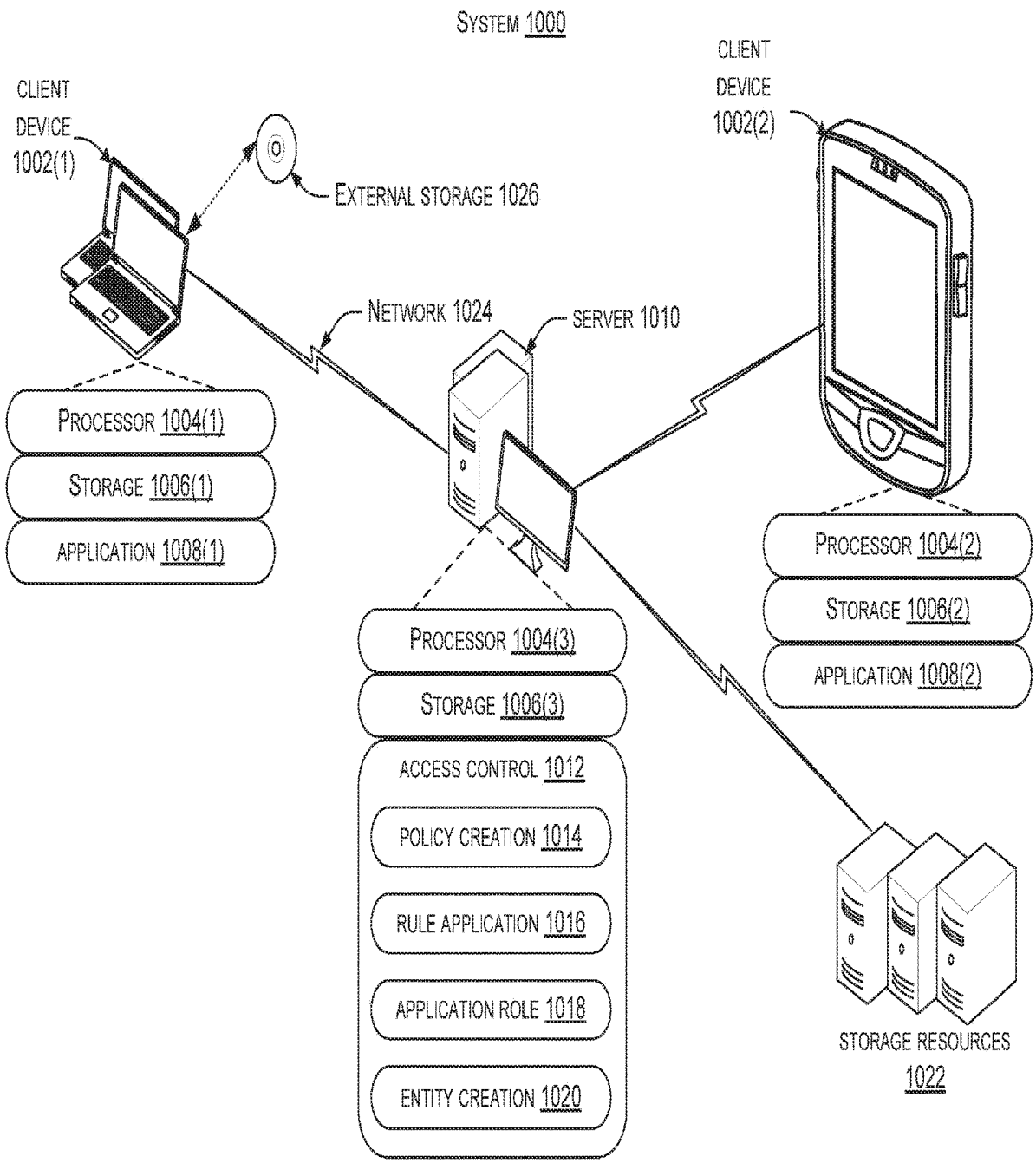
FIG. 10 shows an example of a system in accordance with some implementations of the present concepts.

FIG. 10 shows an example of a system 1000. Example system 1000 includes one or more client device(s) 1002, shown as a notebook client device 1002(1) and a mobile client device 1002(2), respectively. In this case, client device(s) 1002 can each include a processor 1004, storage 1006, and an application 1008. (A suffix '(1)' is utilized to indicate an occurrence of these modules on client device 1002(1) and a suffix '(2)' is utilized to indicate an occurrence on client device 1002(2)).

System 1000 can also include one or more server(s) 1010. Server(s) 1010 can be a computing device that also includes a processor 1004(3) and storage 1006(3). Note the suffix (3) is used to indicate an occurrence of a processor or storage on server 1010. Server 1010 can also include an access control module 1012, which can include submodules such as policy creation module 1014, rule application module 1016, application role module 1018, and entity creation module 1020. System 1000 can also include storage resources 1022, which can include one or more storage devices configured to store the physical database tables mentioned above.

Client device(s) 1002, server 1010, and storage resources 1022 can communicate over one or more networks 1024, such as, but not limited to, the Internet. Applications 1008(1) and 1008(2) and modules 1012-1020 can be implemented as software, hardware, and/or firmware. Processor(s) 1004 can execute data in the form of computer-readable instructions to provide a functionality. Data, such as computer-readable instructions, can be stored on storage 1006. The storage can include any one or more of volatile or non-volatile memory, hard drives, and/or optical storage devices (e.g., CDs, DVDs etc.), among others. Client device(s) 1002 and server 1010 can also be configured to receive and/or generate data in the form of computer-readable instructions from an external storage 1026.

Examples of external storage 1026 can include optical storage devices (e.g., CDs, DVDs etc.), hard drives, and flash storage devices (e.g., memory sticks or memory cards), among others. In some cases, modules discussed herein can be installed on the server during assembly or at least prior to delivery of the server. In other scenarios, the modules discussed herein can be installed after delivery, such as a download available over network 1024 and/or from external storage 1026. The modules discussed herein can be manifest as freestanding applications, application parts and/or part of an operating system. Note also that, in some implementations, individual modules discussed herein can also reside on client devices 1002, e.g., a client device used by a database administrator to perform access control for other client devices.

Collectively, the modules and applications discussed herein can achieve the functionality described above relative to FIGS. 1-9. For example, policy creation module 1014 can be configured to implement method 200, rule application module 1016 can be configured to implement method 400, application role module 1018 can be configured to implement method 600, and entity creation module 1020 can be configured to implement method 900. It is worth noting that in some instances, the client devices or servers can comprise multiple computing devices or machines, such as in a distributed environment. In such a configuration, each of the methods discussed herein can be implemented using distributed processing across the multiple computing devices or machines.

The terms "computer," "client device," "server" and "computing device" as used herein can mean any type of device that has some amount of processing capability and/or storage capability. Processing capability can be provided by one or more processors that can execute data in the form of computer-readable instructions to provide functionality. Data, such as computer-readable instructions, can be stored on storage. The storage can be internal and/or external to the computing device. The storage can include any one or more of volatile or non-volatile memory, hard drives, flash storage devices, and/or optical storage devices (e.g., CDs, DVDs etc.), among others. As used herein, the term "computer-readable media" can include transitory and non-transitory computer-readable instructions. In contrast, the term "computer-readable storage media" excludes transitory instances. Computer-readable storage media includes "computer-readable storage devices". Examples of computer-readable storage devices include volatile storage media, such as RAM, and non-volatile storage media, such as hard drives, optical discs, and flash memory, among others.

Examples of computing devices can include traditional computing devices, such as personal computers, cell phones, smart phones, personal digital assistants, or any of a myriad of ever-evolving or yet to be developed types of computing devices. Further, aspects of system 1000 can be manifest on a single computing device or distributed over multiple computing devices.

In some variations of the illustrated system 1000, each client device 1002 and server 1010 is configured with a general purpose processor 1004 and storage 1006. In other variations, one or more of the server or client devices can include a system on a chip (SOC) type design. For example, functionality provided by the access control module or applications can be integrated on a single SOC or multiple coupled SOCs. In one such example, the computing server or client device can include shared resources and dedicated resources. An interface(s) can facilitate communication between the shared resources and the dedicated resources. As the name implies, dedicated resources can be thought of as including individual portions that are dedicated to achieving specific functionalities. For instance, in this example, the dedicated resources can include the access control module or application.

Shared resources can be storage, processing units, etc. that can be used by multiple functionalities. In this example, the shared resources can include the processor. As mentioned above, the access control module or application can be implemented as dedicated resources. In other configurations, the access control module or application can be implemented on the shared resources and/or the processor can be implemented on the dedicated resources.

CONCLUSION

The order in which the example methods are described is not intended to be construed as a limitation, and any number of the described blocks or steps can be combined in any order to implement the methods, or alternate methods. Furthermore, the methods can be implemented in any suitable hardware, software, firmware, or combination thereof, such that a computing device can implement the methods. In one case, the methods are stored on one or more computer-readable storage media as a set of instructions such that execution by one or more computing devices causes the one or more computing devices to perform the method.

Although techniques, methods, devices, systems, etc., pertaining to secure patient information handling are described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices, systems, etc.

The invention claimed is:

1. A method performed by at least one computer processing device, the method comprising:
    identifying a data source comprising one or more fields from a plurality of data sources;
    creating an access policy including one or more attributes bound to the one or more fields, a view of the data source, and a rule associated with the one or more attributes, wherein the view is a query that indicates a subset of fields from the data source;
    receiving a data request referencing the view;
    in response to the data request, applying the access policy to rewrite the data request to include a JOIN operation on the data source and the view, wherein the rewritten data request limits access to the view in accordance with the rule, and wherein rewriting the query includes rewriting the view to include a query condition comprising a value of the one or more attributes; and
    executing the rewritten data request.

2. The method according to claim 1, further comprising:
    selectively applying the rule to queries on the view by unlocking sensitive data when the one or more attributes of the access policy has a value and locking the sensitive data when the attribute of the access policy does not have the value.

3. The method according to claim 1, further comprising:
    associating one or more user roles with the access policy.

4. The method according to claim 3, further comprising:
    causing the rule to apply to certain users by assigning an individual user role to the individual users.

5. At least one hardware computer-readable storage device having instructions stored thereon that, when executed by one or more computing devices, cause the one or more computing devices to perform acts, the acts comprising:
    identifying a data source comprising one or more fields from a plurality of data sources;
    creating an access policy including one or more attributes bound to the one or more fields, a view of the data source, and a rule associated with the one or more attributes, wherein the view is a query that indicates a subset of fields from the data source;
    receiving a data request referencing the view;
    in response to the data request, applying the access policy to rewrite the data request to include a JOIN operation on the data source and the view, wherein the rewritten data request limits access to the view in accordance with the rule, and wherein rewriting the query includes rewriting the view to include a query condition comprising a value of the one or more attributes; and
    executing the rewritten data request, wherein the executing includes rewriting the view to include a query condition.

6. The at least one hardware computer-readable storage device of claim 5, wherein the data source is a relational database.

7. The at least one hardware computer-readable storage device of claim 5, wherein the query condition is specified in the rewritten view using a WHERE clause having a predicate that includes a value of the one or more attributes.

8. The at least one hardware computer-readable storage device of claim 7, wherein the query condition is specified using structured query language (SQL).

9. The at least one hardware computer-readable storage device of claim 5, wherein the access policy comprises multiple rules that are applied to the view.

10. The at least one hardware computer-readable storage device of claim 5, the acts further comprising:
    receiving another request from another user, the another request including an identifier of a second view included in the access policy; and
    applying the access policy to the second view referenced in the another request for data, wherein applying the access policy to the second view includes rewriting the request for data to include a JOIN operation on the data source and the second view to apply the rule to limit access to one or more values returned via the second view.

11. The at least one hardware computer-readable storage device of claim 5, wherein the user is associated with multiple user roles having multiple associated rules, and the acts further comprise applying each of the multiple associated rules for the multiple user roles associated with the user.

12. A system comprising:
    at least one processing device; and
    at least one storage device storing computer-readable instructions which, when executed by the at least one processing device, cause the processing device to:
        identify a data source comprising one or more fields from a plurality of data sources;
        obtain an access policy including one or more attributes bound to the one or more fields, a view, and a rule associated with the one or more attributes, wherein the view is a query that indicates a subset of fields from the data source;

receive a query referencing the view;

in response to the query, applying the access policy to rewrite the query to include a JOIN operation on the data source and the view, wherein the rewritten data request limits access to the view in accordance with the rule, and wherein rewriting the query includes rewriting the view to include a query condition comprising a value of the one or more attributes; and executing the rewritten query.

13. The system according to claim 12, wherein the data source is a relational database.

14. The system according to claim 12, wherein the rule determines which records of the data source are accessible by a particular user.

15. The system according to claim 14, wherein the rule also determines whether the user can access sensitive attributes of records that are accessible by the particular user.

16. The system according to claim 12, wherein the computer-readable instructions cause the at least one processing device to:

after applying the rule, provide results of the query, wherein one or more requested records are not provided as a consequence of applying the rule.

17. The system according to claim 12, wherein the computer-readable instructions cause the at least one processing device to:

rewrite the view with at least two relational operations on the data source.

18. The system according to claim 17, wherein the at least two relational operations comprise JOIN and SELECT.

19. The method according to claim 1, further comprising:

creating a first entity that is associated with the data source, wherein the first entity is a first collection of data and comprises at least one attribute of the one or more attributes included in the access policy.

20. The method according to claim 19, further comprising:

creating a second entity that is associated with the data source, wherein the second entity is a second collection of data that is different from the first collection of data; and associating the at least one attribute of the first entity with at least one attribute of the second entity such that one or more access controls associated with the at least one attribute of the first entity is inherited by the second entity.

\* \* \* \* \*